(12) United States Patent
Peterson et al.

(10) Patent No.: US 6,193,472 B1
(45) Date of Patent: Feb. 27, 2001

(54) FLUID VACUUM SYSTEM

(75) Inventors: Michael J. Peterson, Nashville; Richard M. Russell, Brentwood, both of TN (US)

(73) Assignee: Dialysis Systems, Inc., Nashville, TN (US)

( * ) Notice: Subject to any disclaimer, the term of this patent is extended or adjusted under 35 U.S.C. 154(b) by 0 days.

(21) Appl. No.: 09/267,515

(22) Filed: Mar. 12, 1999

(51) Int. Cl.[7] ............................ F04B 23/08; B01D 24/00; A61M 1/00
(52) U.S. Cl. .......................... 417/87; 417/148; 210/252; 210/321.71; 604/118; 137/893; 137/565.22; 137/565.23
(58) Field of Search ........................ 417/118, 137, 417/138, 139, 141, 148, 87, 85; 137/888, 893, 565.22, 565.23; 210/252, 232, 321.71, 321.6, 645, 646; 604/118

(56) References Cited

U.S. PATENT DOCUMENTS

| | | |
|---|---|---|
| 3,267,949 | 8/1966 | Adams . |
| 4,114,783 | 9/1978 | Wempe et al. . |
| 4,147,474 * | 4/1979 | Heimdal et al. ............... 417/148 |
| 4,295,346 | 10/1981 | Hoffman . |
| 4,339,232 * | 7/1982 | Campbell ...................... 417/148 |
| 4,370,418 | 1/1983 | Koopman et al. . |
| 4,514,977 * | 5/1985 | Bowen ........................... 417/148 |
| 4,691,731 | 9/1987 | Grooms et al. . |
| 4,793,440 | 12/1988 | Iseman . |
| 4,875,836 | 10/1989 | Zehnder et al. . |
| 4,955,874 | 9/1990 | Farrar et al. . |
| 5,352,097 | 10/1994 | Itou et al. . |
| 5,577,881 | 11/1996 | Hablanian . |
| 5,615,701 | 4/1997 | Yamabe et al. . |
| 5,763,626 | 6/1998 | Guzek et al. . |

* cited by examiner

Primary Examiner—Charles G. Freay
(74) Attorney, Agent, or Firm—Waddey & Patterson; Lucian Wayne Beavers

(57) ABSTRACT

One embodiment of the invention encompasses a fluid vacuum system for vacuuming-up discharge fluid from a fluid source without applying a vacuum to the fluid source. The system comprises a discharge conduit, a vacuum source, and a vacuum-breaker. The discharge conduit is in fluid communication with the fluid source. And, the vacuum-breaker connects the discharge conduit to the vacuum source such that the vacuum source applies a vacuum to the discharge fluid without applying a vacuum to the fluid source. Select embodiments are optimized for use with dialysis machines in dialysis clinics. A closed system, preferably a vacuum system, is provided for disposal of noxious odors and fluids.

37 Claims, 6 Drawing Sheets

FLUID VACUUM SYSTEM

BACKGROUND OF THE INVENTION

The present invention relates generally to a system for transporting fluids from a source of purified water or dialysate to individual dialysis machines in a dialysis clinic.

One objective of the invention is to provide a drain system for fluid discharged from a plurality of dialysis machines. A standard dialysis machine receives ultra pure water with various additives. The combination of water and additives is generally referred to as dialysate. The blood is filtered through the dialysate to remove contaminants. The used dialysate has absorbed these contaminants and is discharged from the dialysis machines as discharge fluid. Traditionally, the discharge fluid is discharged through a floor drain to a city sewer system. Such floor drains are typically expensive to install. Floor drains also often result in the emission of noxious odors. This is particularly so when the substance being dumped through the drain is noxious. This is the case with dialysis discharge fluid.

The drains are sloped which requires substantial elevation changes along the length of the prior art systems. These prior art systems can particularly difficult and expensive to install when rehabilitating an existing building to convert available commercial building space for more intensive clinical use.

It is not possible, however, to directly connect a vacuum system to the discharge line of a dialysis machine. This is because the presence of a vacuum at the dialysis machine will adversely affect the performance of the machine. The importance of maintaining dialysis machine parameters in optimum ranges is discussed in U.S. Pat. No. 5,276,611 entitled "Management Of Parameters Relating To A Dialysis Treatment" by Ghiraldi; and U.S. Pat. No. 5,792,367 entitled "System And Method For Monitoring A Flow Of Dialysis Fluid In A Dialysis Machine" by Mattisson et al., both of which are hereby incorporated herein by reference. The present invention provides the advantages of a vacuum discharge conduit, while preventing the communication of a vacuum to the discharge of the dialysis machine.

What is needed then is a system which facilitates fluid removal without affecting the performance of the fluid source. This needed system must eliminate fluid discharge without applying a vacuum to the source. This needed system should be capable of removing noxious and unsanitary fluid wastes. This needed system should be capable of removing unpleasant odors resulting from the fluid to be removed. This needed system is presently lacking in the prior art.

SUMMARY OF THE INVENTION

The present invention relates to the art of fluid and gas elimination. More particularly, the invention relates to methods and apparatus for applying a vacuum to discharge fluid without applying a vacuum to the discharge fluid source.

One purpose of the present invention is to provide a closed vacuum powered drain system which may be installed within the dialysis treatment clinic. This would also provide for a mobile dialysis treatment clinic. The system may be used to dispose of the discharged fluids without the need for constructing a conventional floor drain system. An additional advantage is that of the elimination of noxious odors associated with the dialysis discharge fluid.

Generally, each of the dialysis machines includes a machine discharge line which connects to a common discharge conduit. The discharge conduit may simply be a length of pipe, preferably plastic pipe, which is mounted along the wall of a room containing the dialysis clinic. It is important to note that the discharge line is a non-pressurized non-vacuum line. Preferably the discharge line is at atmospheric pressure for this embodiment. The discharge from the machines simply drains by gravity, and/or pressure developed at the machine, to the discharge conduit. Preferably the conduit is generally horizontally oriented. A vacuum-breaker is used to prevent the vacuum applied to the fluid from being applied to the dialysis machines.

Accordingly, one embodiment of the invention is for a fluid vacuum system for vacuuming-up a discharge fluid from a fluid source without applying a vacuum to the fluid source. The system comprises a discharge conduit, a vacuum source, and a vacuum-breaker. The discharge conduit is in fluid communication with the fluid source. And, the vacuum-breaker connects the discharge conduit to the vacuum source such that the vacuum source applies a vacuum to the discharge fluid without applying a vacuum to the fluid source.

In a preferred embodiment, the vacuum-breaker comprises a discharge passage, a vent passage, and a transfer passage. The discharge passage is connected to the discharge conduit and the vent passage is communicated with the discharge passage. The transfer passage intersects the discharge passage at a vacuum-breaker junction and extends upward therefrom. The transfer passage is arranged so that when a discharge fluid level in the discharge passage is below the vacuum breaker junction, vented air from the vent passage will break the vacuum in the discharge passage. The transfer passage arrangement also allows discharge fluid to be sucked up through the transfer passage when the discharge fluid level rises above the vacuum-breaker junction.

The invention also encompasses a dialysis clinic comprising a plurality of dialysis machines, a discharge conduit, a vacuum source, a vacuum conduit, and a vent. The plurality of dialysis machines discharge a respective plurality of streams of discharge fluid. The discharge conduit is connected to the dialysis machines to receive the discharge fluid. The vacuum conduit is communicated with the discharge conduit and extends upwardly therefrom. The vacuum conduit is also connected to the vacuum source. The vent is connected to the discharge conduit and the vacuum conduit at a junction. When the level of discharge fluid in the discharge conduit is below the junction air will flow through the vent to the vacuum conduit and prevent a vacuum in the discharge conduit.

In another embodiment of the invention, the vacuum-breaker apparatus comprises a manifold block. The manifold block has defined therein a horizontal discharge passage; a vertical vacuum passage intersecting the discharge passage; and a vertical vent passage intersecting the discharge passage.

It will be apparent to those of skill in the art that the present invention comprises various methods for transporting and disposing of liquid. One such method of disposing of liquid comprises the steps of: discharging the liquid from a dialysis machine into a discharge conduit; conducting the liquid through the discharge conduit to a vacuum-breaker; and applying a vacuum to the liquid above a predetermined elevation in the vacuum-breaker. The method also includes, in select embodiments, the step of preventing the dialysis machine from being acted upon by the vacuum.

Accordingly, an object of the present invention is to provide methods and devices for eliminating fluid discharge without applying a vacuum the fluid sources. A further objective is to optimize embodiments for use where the fluid source is bio-equipment. A further objective is to provide these methods and devices for use with dialysis machines.

Another object of the invention is to provide means and methods for reducing or eliminating unpleasant odors associated with bio-equipment discharge fluid. A further objective is to reduce the release of airborne pathogens in sensitive areas. The sensitive areas may include patient treatment areas such as clinics, Yet another objective is to provide a biohazard venting system.

Another objective is to provide means and methods for removing bio-equipment fluid discharge without effecting the performance of the bio-equipment.

One objective is to provide a closed discharge system for a bio-facility. A further objective is to provide a closed-vacuum system for a dialysis clinic.

A further objective is to provide methods and means of converting a room, or building, into a health care facility, particularly a dialysis clinic. A further objective is to avoid or reduce the expense of installing permanent plumbing fixtures.

Another objective is to eliminate the need to slope piping to drain fluid by gravity.

Another objective is to provide a mobile health care facility.

Another objective is to provide a relatively convenient way of disinfecting or replacing plumbing for a health care facility.

Other objects and advantages of the invention will be apparent to those of skill in the art from the teachings disclosed herein, including the attached drawings and claims.

DESCRIPTION OF THE PREFERRED EMBODIMENTS

Figure 1:
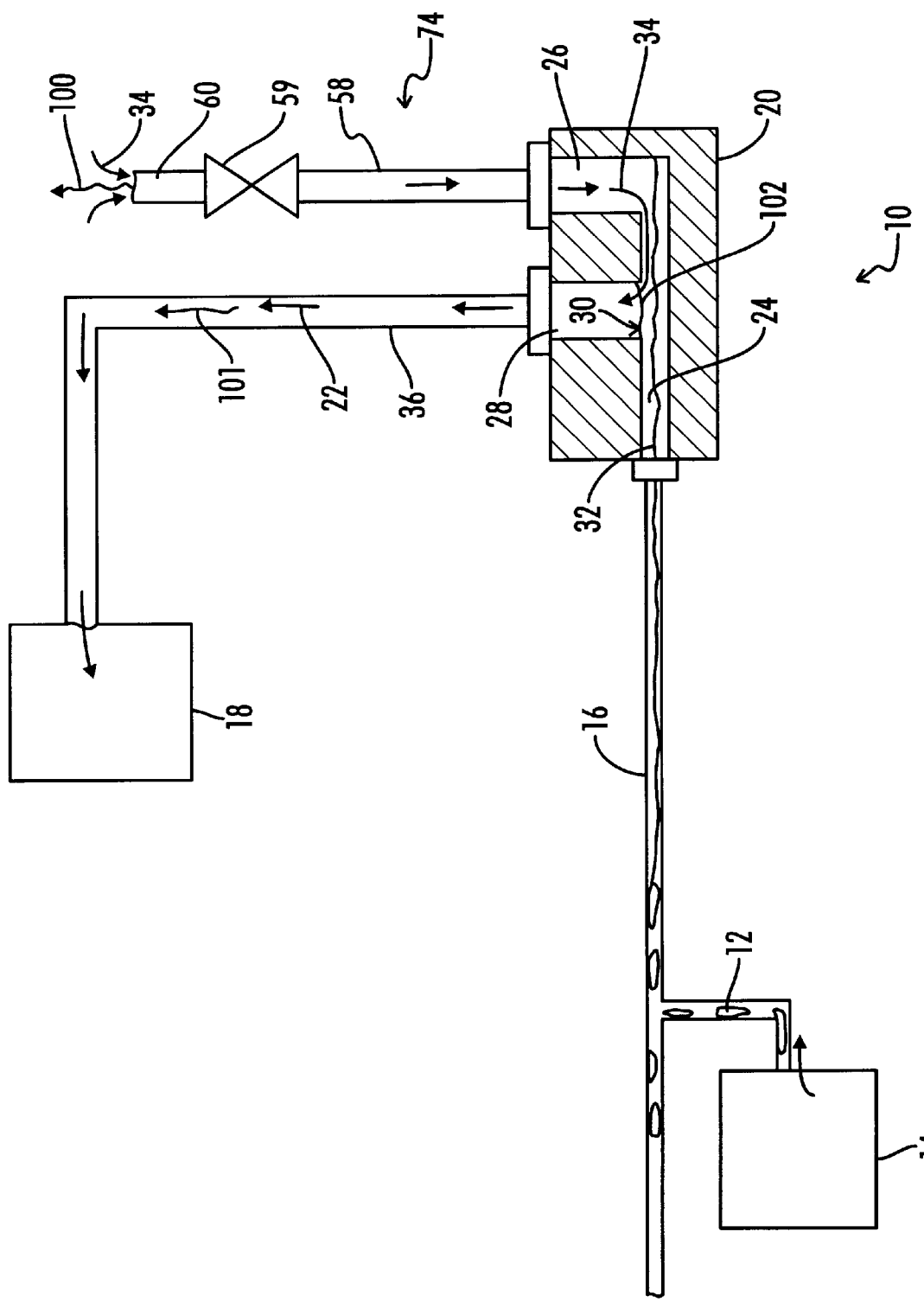
FIG. 1 depicts a fluid vacuum system of the present invention. A section view of the vacuum-breaker is shown. The system is shown venting air.

The present invention relates to fluid transport systems. More particularly the present invention relates to fluid systems for vacuuming-up discharge fluid. Removal of gases is provided for as well. The present invention will be readily understood from the following teachings with reference to the attached drawings wherein like reference numerals refer to like components.

FIG. 1 depicts a fluid vacuum system 10 encompassed by the present invention. The fluid system 10 is for vacuuming-up a discharge fluid 12 from a fluid source 14 without applying a vacuum to the fluid source 14. The system 10 shown in FIG. 1 comprises a discharge conduit 16 in fluid communication with the fluid source 14. The system 10 also comprises a vacuum source 18 and a vacuum-breaker 20. The vacuum-breaker 20 connects the discharge conduit 16 to the vacuum source 18 such that the vacuum source 18 applies a vacuum 22 to the discharge fluid 12 without applying a vacuum to the fluid source 14. This is shown well in FIG. 2 wherein discharge fluid 12 in the vacuum-breaker 20 is drawn upward by the application of the vacuum 22.

The system 10 is preferably a portable system like that disclosed in our pending U.S. patent application Ser. No. 09/065,780, titled "System for Fluid Delivery in a Dialysis Clinic", filed Dec. 7, 1998, the details of which are incorporated herein by reference. The discharge conduit 16 may for example be located in the position of conduit 132 seen in FIG. 13 of the aforesaid application.

Figure 2:
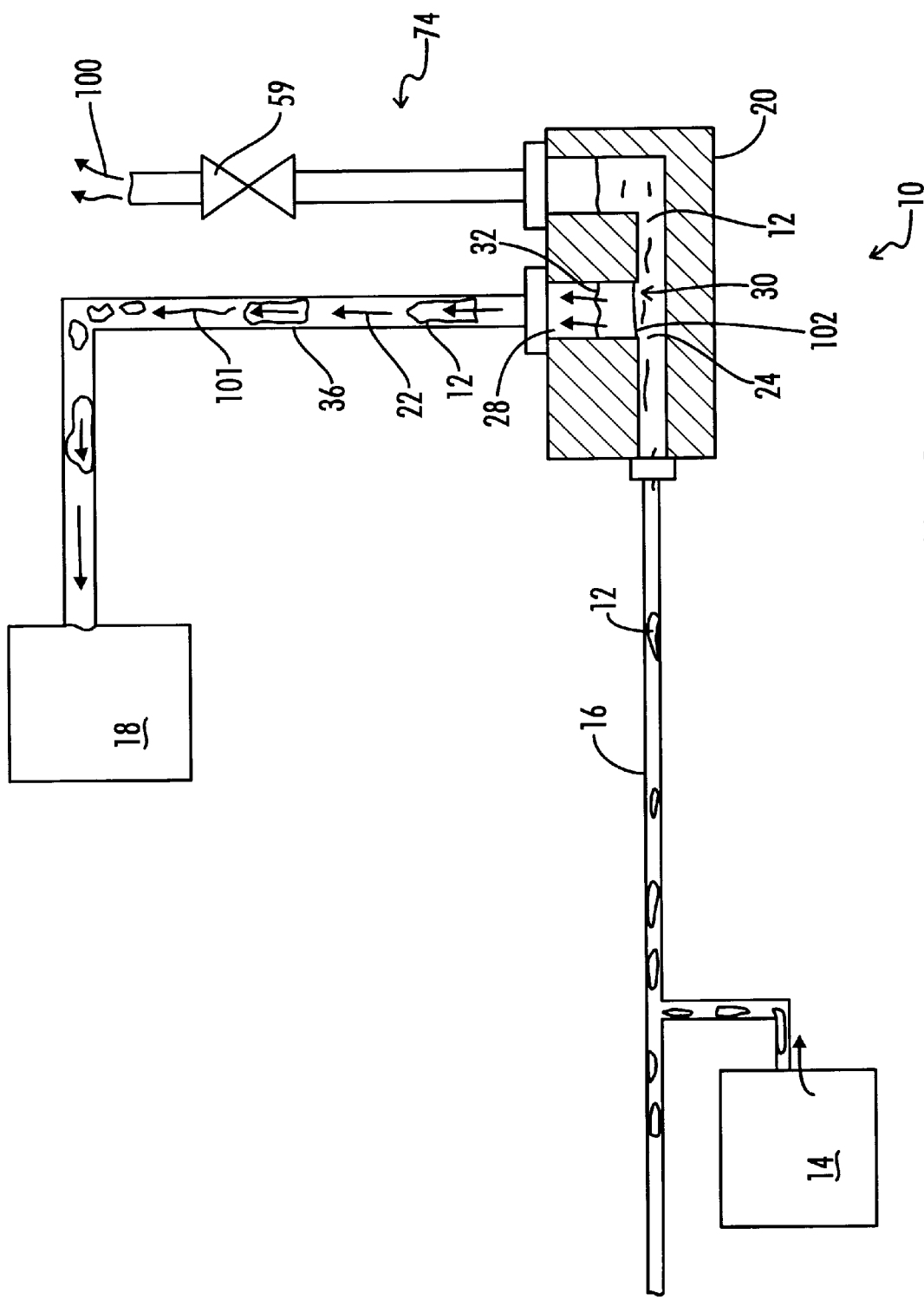
FIG. 2 depicts the system shown in FIG. 1 vacuuming-up discharge fluid. The fluid is above the breaker junction.
Figure 3:
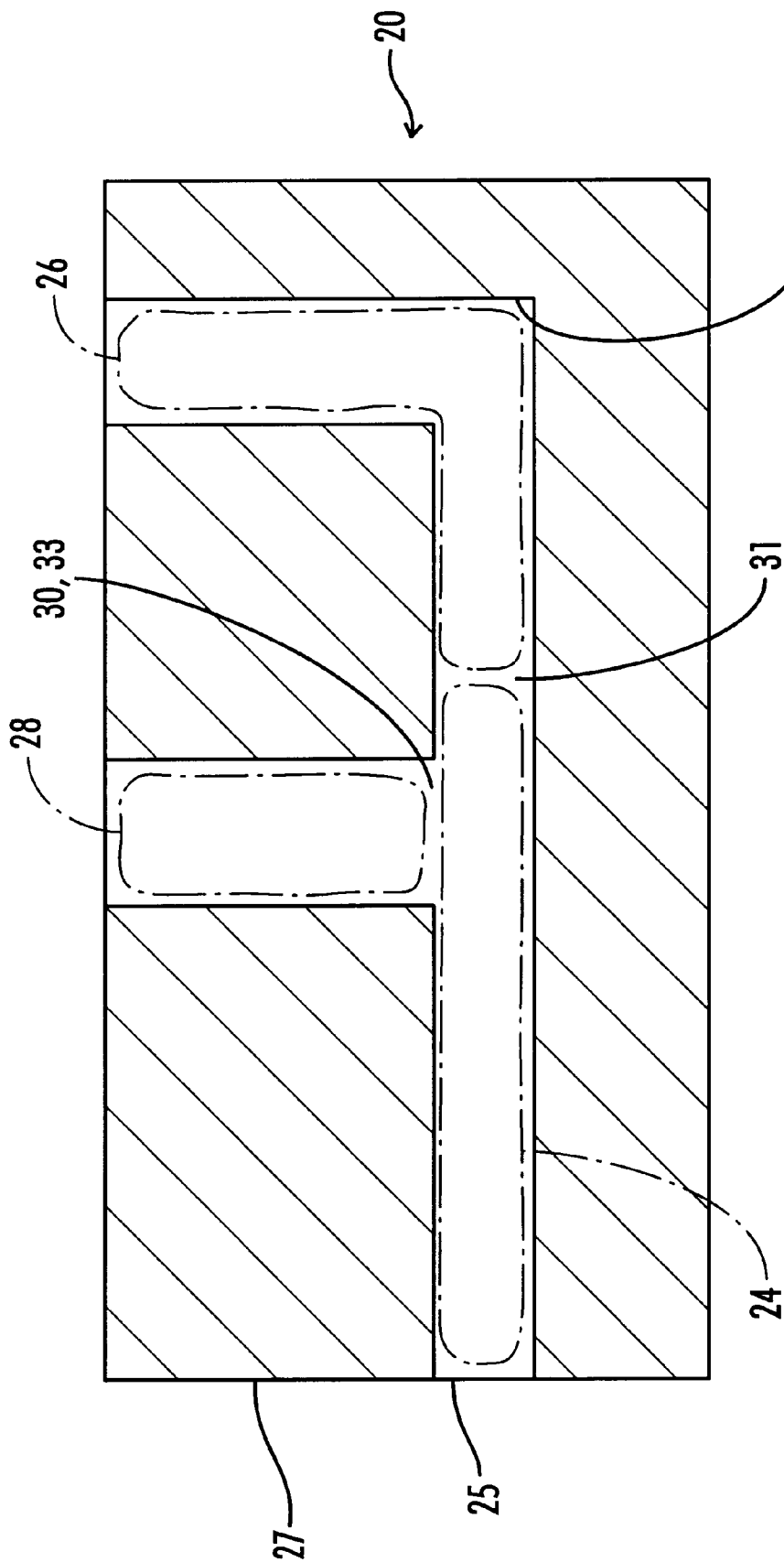
FIG. 3 shows a cross-section of the vacuum-breaker. The discharge, transfer, and venting passages are indicated generally with phantom lines.

FIG. 3 depicts the vacuum-breaker 20 shown in FIGS. 1 and 2. The embodiment of the vacuum-breaker depicted in FIGS. 1–3 comprises a discharge passage 24, a vent passage 26, and a transfer passage 28. Phantom lines are used to show the general area of the passages in FIG. 3. The discharge passage 24 is connected to the discharge conduit 16 (not shown in FIG. 3). The vent passage 26 is communicated with the discharge passage 24. The transfer passage 28 intersects the discharge passage 24 at a vacuum-breaker junction 30 and extends upward therefrom. This is so that when a discharge fluid level 32 in the discharge passage 24 is below the vacuum-breaker junction 30, vented air 34 from the vent passage 26 will break the vacuum 22 in the discharge passage 24. This is shown in FIG. 1. Referring now to FIG. 2, when the discharge fluid level 32 rises above the vacuum-breaker junction 30, the discharge fluid 12 is pushed up through the transfer passage 28 toward the lower pressure.

In one embodiment of the vacuum-breaker 20, the discharge passage 24 is horizontal and intersects the transfer passage 28. The transfer passage 28 is vertical in some embodiments, as is the vent passage 26. Referring to the vacuum-breaker 20 shown in FIG. 3, the discharge passage 24 has an open inlet end 25 defined by a surface 27 of the vacuum-breaker 20. A blind end 29 is defined internally. The vent passage 26 intersects the discharge passage 24 at a first location 31. The transfer passage 28 intersects the discharge passage 24 at a second location 33. The second location 33 is between the open inlet 25 and the first location 31. In select embodiments, the vacuum-breaker 20 is made of plastic material. In some preferred embodiments, the vacuum-breaker 20 is made from a solid block.

Figure 7:
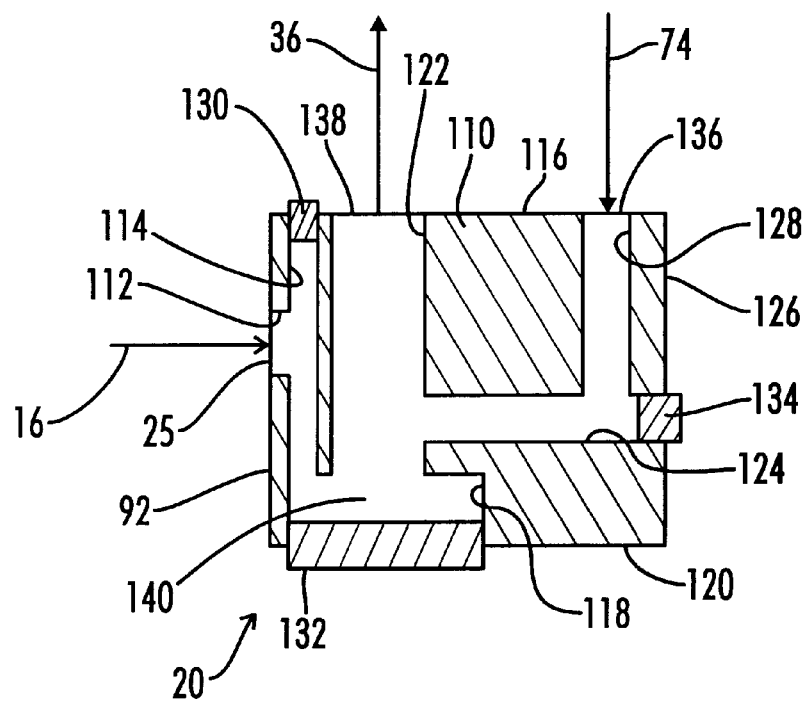
FIG. 7 shows a section view of still another embodiment of a vacuum-breaker.

FIG. 7 schematically illustrates a preferred embodiment of the vacuum-breaker 20 made from a solid block of material. The various passages are formed by a plurality of bores into the block.

Inlet 25 is formed by a short bore 112 extending into surface 92.

A vertical bore 114 extends into top surface 116 and intersects the short horizontal bore 112.

A larger vertical bore 118 extends into bottom surface 120.

Another vertical bore 122 extends downward from top surface 116 and intersects the lower vertical bore 118.

Another horizontal bore 124 is formed in the right end surface 126 of block 10 and intersects the vertical bore 122.

Another vertical bore 128 extends downward from top surface 116 and intersects the horizontal bore 124.

The upper end of bore 114 is closed by a first threaded plug 130. The lower end of vertical bore 118 is closed by a second threaded plug 132. The right end of horizontal bore 124 is closed by a third threaded plug 134.

The discharge conduit 16 connects to the horizontal bore 112 by a threaded connection at inlet 25.

The vent line 74 is connected to vertical bore 128 at vent inlet 136 at a threaded connection. The vacuum line 36 is connected to vertical bore 122 by a threaded connection at vacuum outlet 138.

Plugs 132 and 134 serve as drain plugs for the vacuum-breaker 20.

The upper portion 140 of vertical bore 118 and the adjoining lower end portions of vertical bores 114 and 122 form an accumulator cavity 140. It will be appreciated that as discharge fluid flows through discharge line 16 into the vacuum-breaker 20 it must fill the accumulator cavity 140 to a level rising above the horizontal bore 124 before a slug of fluid will be carried up through the vacuum line 36.

Figure 4:
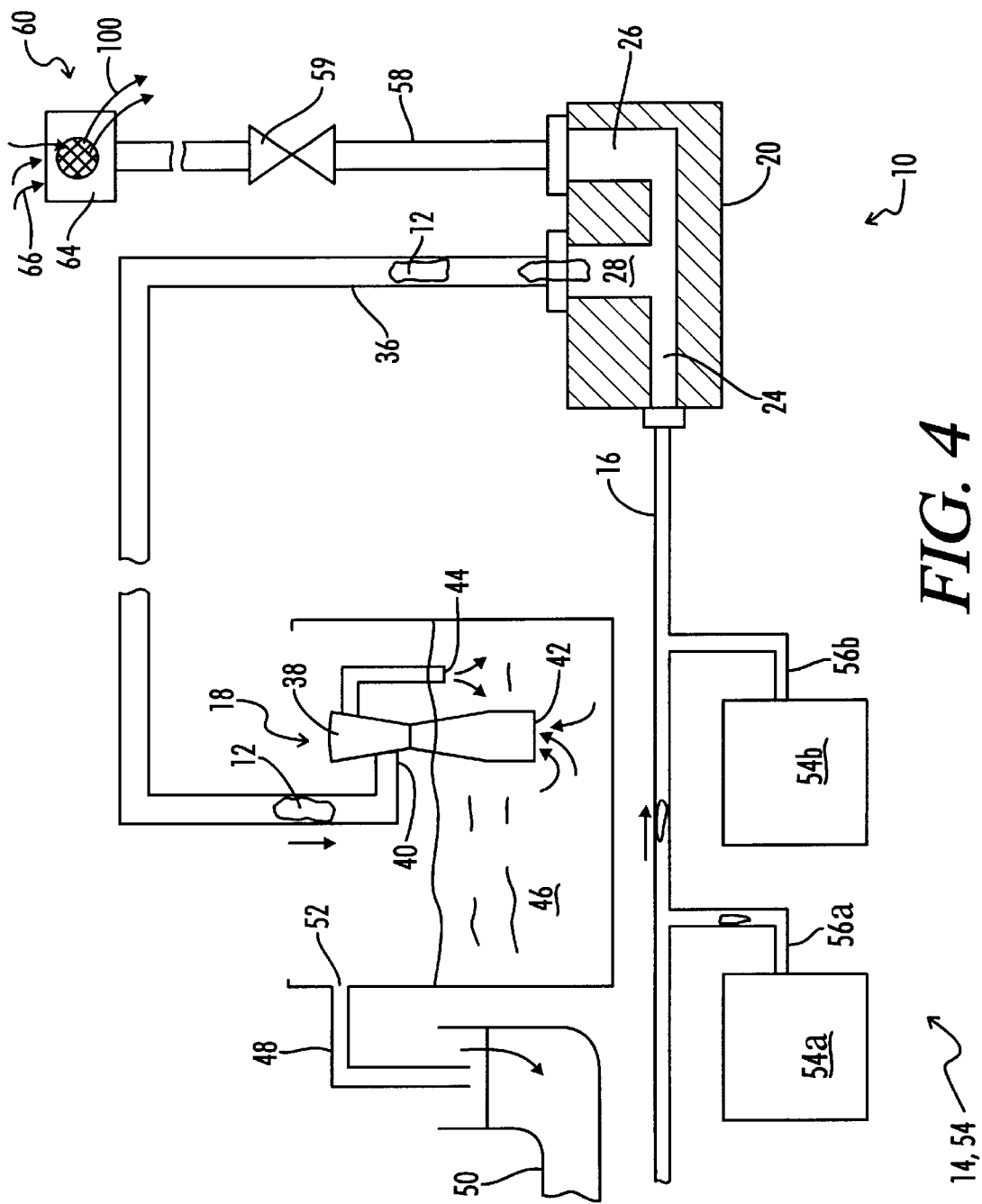
FIG. 4 is similar to the system shown in FIG. 1 with additional components depicted. A pump is shown as the vacuum source and an air check valve/vent cap prevents obstructions from entering the venting conduit and noxious gases from escaping.

FIG. 4 depicts an embodiment of the system 10 comprising a vacuum conduit 36 connecting the transfer passage 28 to the vacuum source 18. In one preferred embodiment the vacuum source is a pump 38.

In one preferred embodiment the pump 38 is an eductor pump having a vacuum port 40 connected to the vacuum conduit 36. An inlet 42 and an outlet 44 are in operable relation to allow the pump 38 to operate and apply a vacuum 22 to the vacuum port 40. The pump inlet 42 is submerged in a sump of fluid 46. The pump 38 circulates fluid in the sump 46 up through the pump inlet 42 and out through the pump outlet 44 whereby a vacuum is created across the vacuum port 40 by the pump 38 and whereby the pump 38 draws discharge fluid 12 through the vacuum conduit 36. This is shown in FIG. 4.

An example of an eductor pump is disclosed in U.S. Pat. No. 4,114,783 by Wente, et al. which is hereby incorporated herein by reference. An example of another vacuum source is disclosed in U.S. Pat. No. 5,352,097 by Itou, et al., which is hereby incorporated herein by reference. Other acceptable vacuum sources will be apparent to those of skill in the art from the teachings disclosed herein.

Generally, the eductor pump is of a standard design and works in a standard manner. The eductor pump is typically powered by an electrically driven centrifugal pump which inducts in fluid from the sump 46 through the inlet 42 and forces the liquid out the outlet 44. The liquid moving rapidly from the inlet 42 to the outlet 44 past the vacuum port 40 creates a vacuum on the vacuum conduit 36. Thus, if there is no fluid 12 in the discharge conduit 16, the pump 38 will simply circulate fluid in the sump 46, e.g.: in the inlet 42 out the outlet 44, into the sump 46, and in the inlet 42, and so on.

The system 10 shown in FIG. 4 comprises an overflow pipe 48 exiting into a sewer 50. The sump 46 has an overflow exit 52 connected to the overflow pipe 48.

In the system 10 shown in FIG. 4 the fluid source 14 is a plurality of dialysis machines 54. Two machines are designated 54a and 54b. Each dialysis machine has respective discharge lines 56a and 56b fluidly connected to the discharge conduit 16.

In one preferred embodiment of the system 10, the discharge conduit 16 is inclined relative to a horizontal surface (not shown) so as to gravity feed the discharge fluid 12 to the discharge passage 24. The discharge conduit may, however, be horizontal or even slightly upwardly inclined toward vacuum-breaker 20.

In the embodiment of the vacuum-breaker 20 shown in FIG. 4, the discharge passage 24 is horizontal and the transfer passage 28 is vertical. Other embodiments of the vacuum-breaker will be apparent to those of skill in the art from teachings disclosed herein.

In some embodiments the system 10 further comprises a venting conduit 58 connected to the vent passage 26 and having a venting conduit inlet 60 located outside a room 62 containing the fluid source 14. This is shown in FIG. 5.

Figure 5:
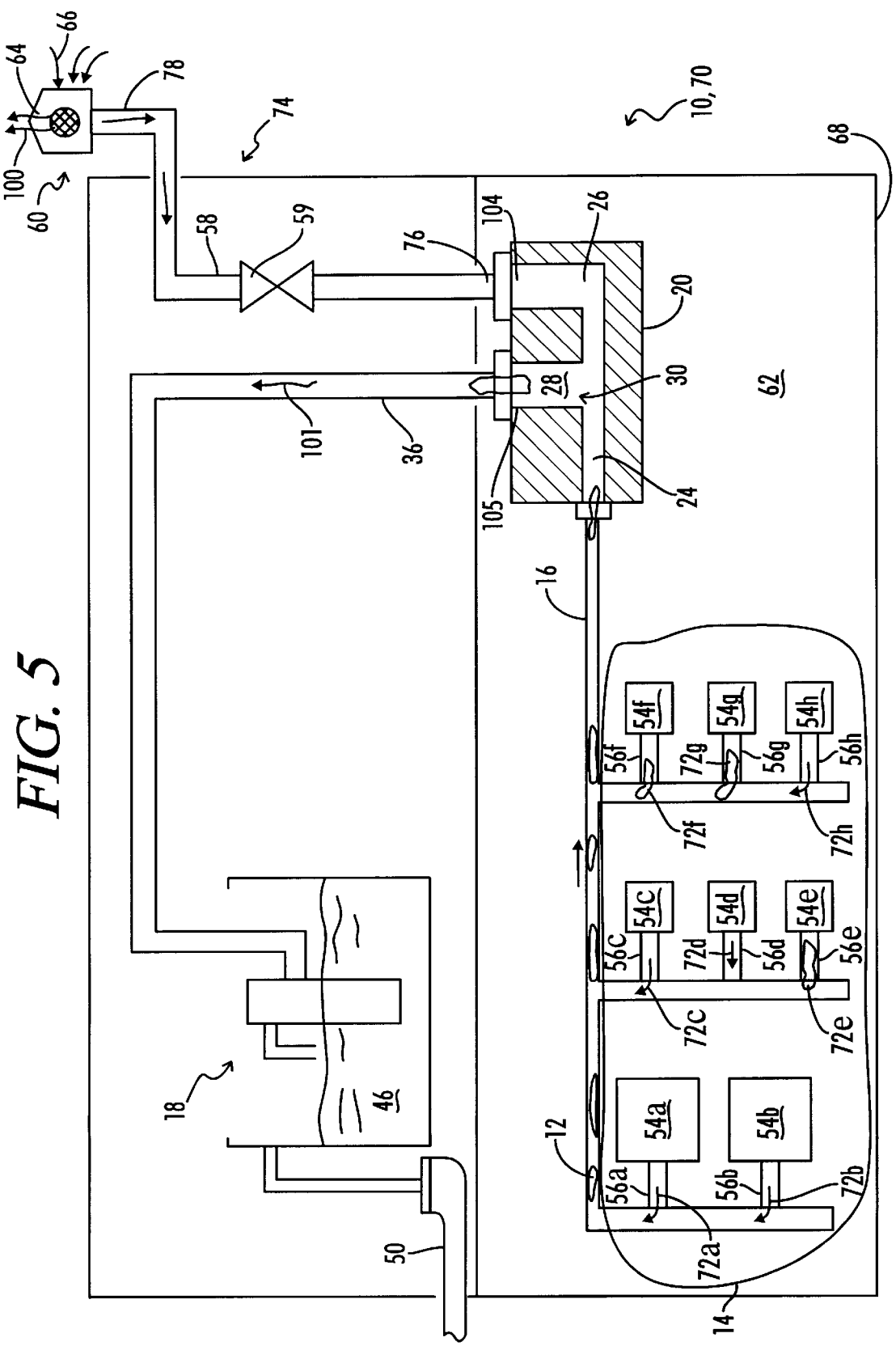
FIG. 5 depicts a dialysis clinic wherein the pump and vent are located outside a room containing the dialysis machines. The vent cap is located outside of the building.

In the embodiment shown in FIGS. 4 and 5, the venting conduit inlet 60 has a cap 64 allowing air 66 to pass into this system while preventing obstructing articles (not shown) from blocking the venting conduit inlet 60 or allowing noxious gases to escape. The air 66 is also referred to herein as vented air 34. In the embodiments of the system 10 shown in FIG. 5, the venting conduit inlet 60 is located outside a building 68 housing the fluid source 14.

The vent conduit 58 has a balancing valve 59 disposed therein. The balancing valve 59 is used to control the rate of flow of vent air downward through the vent line 58. It will be appreciated that if the balancing valve 59 is open too widely, then too much air will flow through the vent line and up through the vacuum line 36 thus effectively preventing the discharge line 16 from sensing the presence of the low pressure or vacuum in vacuum line 36. By partially closing the balancing valve 59 the flow of vent air downward there through will be reduced until the discharge fluid in discharge line 16 begins to be picked up into the vacuum conduit 36. Once the balancing valve 59 has been manually set to the appropriate setting, further attention is usually unnecessary and the system will remain balanced so that when fluid is present in discharge conduit 16 it will be picked up in slugs and flow upward through the vacuum conduit 36.

The fluid source 14 shown in FIG. 5 includes a plurality of dialysis machines designated 54a–54h having respective discharge lines designated 56a–56h fluidly connected to the discharge conduit 16.

The system 10 includes an embodiment wherein the vacuum-breaker comprises a transfer passage 28 communicated with the vacuum source 18. In some embodiments the discharge fluid 12 is gravity fed to the transfer passage 28 from the discharge conduit 16. The discharge fluid 12 may be vacuum transferred from the transfer passage 28 to a sump 46.

Thus, as waste water (also referred to herein as discharge fluid) 12 is discharged from the dialysis machines 54, it flows through the discharge conduit 16. As the water fills the discharge conduit, it will cover the opening between the discharge passage 24 and the transfer passage 28, i.e. at the junction 30. Once the opening is covered, a column of fluid builds up within the transfer passage 28. The column of fluid is generally very small, on the order of only a few inches. The vacuum 22 is applied to this column of fluid and a slug of fluid is pushed up through the vacuum conduit 36 to be dumped into the sump 46. The flow of liquid up through the vacuum conduit 36 is generally a two phase flow mixture of air and discharge fluid 12.

The present invention also encompasses a dialysis clinic 70. FIG. 5 depicts an embodiment of the system 10 which is a dialysis clinic 70. The dialysis clinic 70 depicted in FIG. 5 comprises a plurality of dialysis machines designated 54a–54h discharging a respective plurality of streams of discharge fluid designated 72a–72h. A discharge conduit 16 is connected to the dialysis machines 54 to receive the discharge fluid, which is designated generally as 12.

The clinic 70 also comprises a vacuum source 18 and a vacuum conduit 36 connected to the vacuum source 18. The vacuum conduit 36 is communicated with the discharge conduit 16 and extends upwardly therefrom. A vent 74 is connected to the discharge conduit 16 and the vacuum conduit 36 at a junction 30 so that when a level of the discharge fluid (shown in FIG. 2 as reference number 32) in the discharge conduit 16 is below the junction 30, air 66 will flow through the vent 74 to the vacuum conduit 36 and prevent a vacuum 22 in the discharge conduit 16.

The clinic 70 shown in FIG. 5 utilizes a vacuum-breaker manifold 20. FIG. 3 shows an enlarged cross-sectional view of the vacuum-breaker manifold 20. In the embodiment shown in FIG. 3 the vacuum-breaker 20 includes a horizontal discharge passage 24 connected to the discharge conduit (not shown in FIG. 3) and a vertical transfer passage 28 intersecting the discharge passage 24. The vertical transfer passage 28 is connected to the vacuum conduit 36 (shown in FIG. 5). A venting passage 26 connects the vent 74 to the discharge passage 24 and the transfer passage 28.

In one embodiment of the clinic 70, the vent 74 includes a venting conduit 58 having a first end 76 connected to the junction 30 and a second end 78 opening external to the clinic building 68. The clinic building 68 is also referred to herein as a building 68 housing a fluid source 14.

Figure 6:
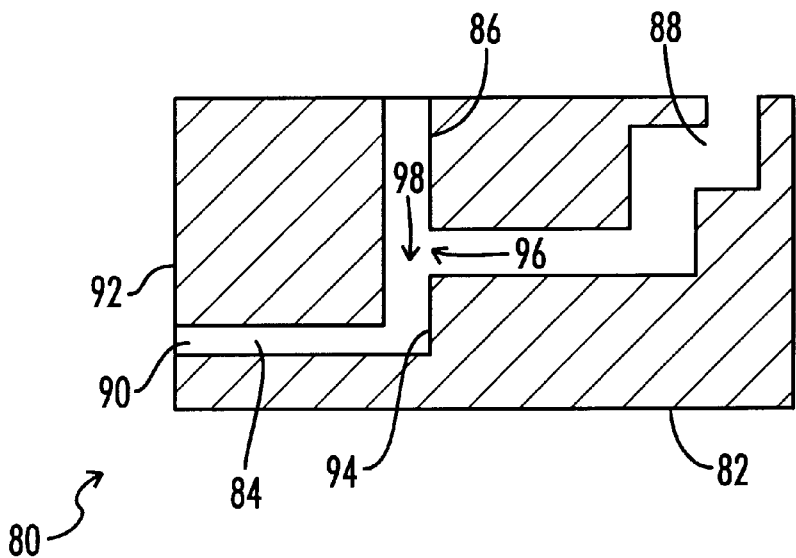
FIG. 6 shows a section view of another embodiment of a vacuum-breaker.

FIG. 6 shows an alternative embodiment of a vacuum-breaker apparatus 80. The vacuum-breaker apparatus 80 comprises a manifold block 82. The manifold block 82 has defined therein a horizontal discharge passage 84; a vertical vacuum passage 86 intersecting the discharge passage 84; and a vertical vent passage intersecting the discharge passage 84.

In the embodiment shown in FIG. 6, the discharge passage 84 has an open inlet end 90 defined in an external surface 92 of the manifold block 82. A blind end 94 is defined internally within the manifold block 82. The vent passage 88 intersects the discharge passage 84 at a first location 96. The vacuum passage 86 intersects the discharge passage 84 at a second location 98. The second location 98 is between the open inlet 90 and the first location 96. In one preferred embodiment the manifold block 82 is constructed from a solid block of plastic material. Thus, discharge fluid in discharge passage 84 will not be drawn up into vacuum passage 86 until the fluid level rises above the intersection 96.

Noxious odors 100 and 101 associated with the discharge fluid 12 will be vented out through the vent 74 and vacuum conduit 36, respectively. (See FIGS. 1 and 2).

It will be apparent to those of skill in the art that the present invention also includes methods of disposing of liquid. One such method comprises the steps of discharging the liquid 12 from a dialysis machine 54 into a discharge conduit 16 and conducting the liquid 12 through the discharge conduit 16 to a vacuum-breaker 20. A vacuum 18 is applied to the liquid 12 above a predetermined elevation 102 (see FIG. 2) in the vacuum-breaker 20. Preferably, the method includes preventing the dialysis machine 54 from being acted upon by the vacuum 18.

Generally, the method includes maintaining atmospheric pressure in the discharge conduit 16. In preferred embodiments, noxious odors 100 and 101 associated with the fluid 12 are vented through vents 104 and 105 in the vacuum-breaker 20. FIG. 5 shows a method of venting the noxious odors 100 and 101 external to a room 62 containing the fluid source 14. In select preferred embodiments, the fluid source 14 is a plurality of dialysis machines 54. However, it will be apparent to those skilled in the art that the fluid source may be any conventional bio-equipment producing discharge fluid 12. All or most odor (e. g. odor 101) would go with the airflow to the sump 46. There it may be filtered and/or dissipated and then removed to the sewer 50.

A method of drawing in air 34 through a vent 74 when the fluid 12 is below the predetermined elevation 102 as shown in FIG. 1. (Air 34 is also referred to as air 66).

Thus, although there have been described particular embodiments of the present invention of a new and useful A Fluid Vacuum System, it is not intended that such references be construed as limitations upon the scope of this invention except as set forth in the following claims.

What is claimed is:

1. A fluid vacuum system for vacuuming-up a discharge fluid from a fluid source without directly applying a vacuum to the fluid source, the system comprising:

a substantially horizontal discharge conduit in fluid communication with the fluid source;

a vacuum source; and a vacuum-breaker connecting the discharge conduit to the vacuum source such that the vacuum source applies a vacuum to the discharge fluid and such that the vacuum-breaker prevents direct application of the vacuum to the fluid source.

2. The system of claim 1, wherein the vacuum source is an eductor pump.

3. A fluid vacuum system for vacuuming up a discharge fluid from a fluid source without directly applying a vacuum to the fluid source, the system comprising:

a discharge conduit in fluid communication with the fluid source;

a vacuum source;

a vacuum-breaker connecting the discharge conduit to the vacuum source such that the vacuum source applies a vacuum to the discharge fluid and such that the vacuum breaker prevents direct application of the vacuum to the fluid source, the vacuum-breaker including:

a discharge passage connected to the discharge conduit;

a vent passage communicated with the discharge passage; and a transfer passage intersecting the discharge passage at a vacuum-breaker junction and extending upward therefrom, so that when a discharge fluid level in the discharge passage is below the vacuum breaker junction vented air from the vent passage will break the vacuum in the discharge passage, and so that when the discharge fluid level rises above the vacuum-breaker junction the discharge fluid is pushed up through the transfer passage.

4. The system of claim 3, comprising a vacuum conduit connecting the transfer passage to the vacuum source.

5. The system of claim 4, wherein the vacuum source is a pump.

6. The system of claim 5, wherein:

the pump is an eductor pump having a vacuum port connected to the vacuum conduit, and an inlet and an outlet in operable relation to allow the pump to operate and apply a vacuum to the vacuum port;

the pump inlet is submerged in a sump of fluid; and the pump circulates fluid in the sump up through the pump inlet and out through the pump outlet and draws discharge fluid through the vacuum conduit.

7. The system of claim 6, comprising:
an overflow pipe exiting into a sewer; and wherein
the sump has an overflow exit connected to the overflow pipe.

8. The system of claim 3, wherein the fluid source is a plurality of dialysis machines having respective discharge lines fluidly connected to the discharge conduit.

9. The system of claim 8, wherein the discharge conduit is inclined relative to a horizontal surface so as to gravity feed the discharge fluid to the discharge passage.

10. The system of claim 3, wherein the discharge passage is horizontal and the transfer passage is vertical.

11. The system of claim 3, further comprising a venting conduit connected to the vent passage and having a venting conduit inlet located outside a room containing the fluid source.

12. The system of claim 4, further comprising a balancing valve disposed in the venting conduit.

13. The system of claim 4, wherein the venting conduit inlet has an air check valve allowing air to pass in one direction only while preventing obstructing articles from blocking the venting conduit inlet and preventing noxious gases from escaping.

14. The system of claim 13, wherein the venting conduit inlet is located outside a building housing the fluid source.

15. A dialysis clinic comprising:
a plurality of dialysis machines discharging a respective plurality of streams of discharge fluid;
a discharge conduit connected to the dialysis machines to receive the discharge fluid;
a vacuum source;
a vacuum conduit communicated with the discharge conduit and extending upwardly therefrom, the vacuum conduit being connected to the vacuum source; and
a vent connected to the discharge conduit and the vacuum conduit at a junction so that when a level of discharge fluid in the discharge conduit is below the junction air will flow through the vent to the vacuum conduit and prevent a vacuum in the discharge conduit.

16. The clinic of claim 15, further comprising a vacuum-breaker manifold which includes:
a horizontal discharge passage connected to the discharge conduit;
a vertical transfer passage intersecting the discharge passage and connected to the vacuum conduit; and
a venting passage connecting the vent to the discharge passage and the transfer passage.

17. The clinic of claim 15, wherein the vent includes a venting conduit having a first end communicated with the junction and a second end opening external to the clinic building.

18. The clinic of claim 17, further comprising a balancing valve disposed in the venting conduit.

19. The clinic of claim 15, wherein the vacuum source is an eductor pump in a sump.

20. The clinic of claim 19, wherein the sump has an overflow port and an overflow conduit exiting to a sewer.

21. A vacuum-breaker apparatus, comprising a manifold block having defined therein:
a horizontal discharge passage;
a vertical vacuum passage intersecting the discharge passage; and
a vertical vent passage intersecting the discharge passage.

22. The apparatus of claim 21, wherein:
the discharge passage has an open inlet end defined in an external surface of the manifold block, and a blind end defined internally within the manifold block; and
the vent passage intersects the discharge passage at a first location, and the vacuum passage intersects the discharge passage at a second location between the open inlet and the first location.

23. The apparatus of claim 21, wherein the manifold block is constructed from a solid block of plastic material.

24. A method of disposing of liquid comprising the steps of:
discharging the liquid from a fluid source into a discharge conduit;
conducting the liquid substantially horizontally through the discharge conduit to a vacuum-breaker;
applying a vacuum to the liquid above a predetermined elevation in the vacuum-breaker; and
preventing the fluid source from being directly acted upon by the vacuum.

25. The method of claim 24, comprising maintaining atmospheric pressure in the discharge conduit.

26. The method of claim 24, comprising venting noxious odors associated with the fluid.

27. The method of claim 26, wherein the noxious odors are vented external of a room containing the fluid source.

28. The method of claim 24, comprising the step of drawing air through a vent when the fluid is below the predetermined elevation.

29. The method of claim 28, further comprising the step of adjusting a balancing valve to control the flow of air to the vent so that the liquid is drawn from the vacuum-breaker.

30. The method of claim 24, wherein the conducting step comprises gravity feeding the fluid to the vacuum-breaker.

31. The method of claim 24, further comprising the steps of:
vacuuming up a slug of fluid through a vacuum conduit and moving the slug toward a pump; and
dumping the slug of discharge fluid into a sump.

32. The method of claim 31, further comprising the step of draining overflow from the sump into a sewer.

33. A fluid vacuum system for vacuuming up a discharge fluid from a fluid source without directly applying a vacuum to the fluid source, the fluid source including a plurality of dialysis machines having respective discharge lines, the system comprising:
a discharge conduit fluidly connected to the respective discharge lines of the plurality of dialysis machines;
a vacuum source; and
a vacuum breaker connecting the discharge conduit to the vacuum source such that the vacuum source applies a vacuum to the discharge fluid and such that the vacuum breaker prevents direct application of vacuum to the dialysis machines.

34. The system of claim 33, wherein the vacuum-breaker comprises a transfer passage communicated with the vacuum source; and wherein the discharge fluid is gravity fed to the transfer passage from the discharge conduit.

35. The system of claim 34, wherein the discharge fluid is vacuum transferred from the transfer passage to a sump.

36. A method of disposing of liquid comprising the steps of:
discharging the liquid from a fluid source into a discharge conduit;
conducting the liquid through the discharge conduit to a vacuum breaker;
applying a vacuum to the liquid above a pre-determined elevation in the vacuum breaker;
preventing the fluid source from being directly acted upon by the vacuum;

drawing air through a vent when the fluid is below the pre-determined elevation; and adjusting a balancing valve to control the flow of air to the vent so that the liquid is drawn from the vacuum breaker.

37. A method of disposing of liquid comprising the steps of:

discharging the liquid from a fluid source into a discharge conduit;

conducting the liquid through the discharge conduit to a vacuum breaker;

applying a vacuum to the liquid above a pre-determined elevation in the vacuum breaker;

preventing the fluid source from being directly acted upon by the vacuum;

vacuuming up a slug of fluid through a vacuum conduit and moving the slug toward a pump;

dumping the slug of discharge fluid into a sump; and draining overflow from the sump into a sewer.

* * * * *